Figure 1:
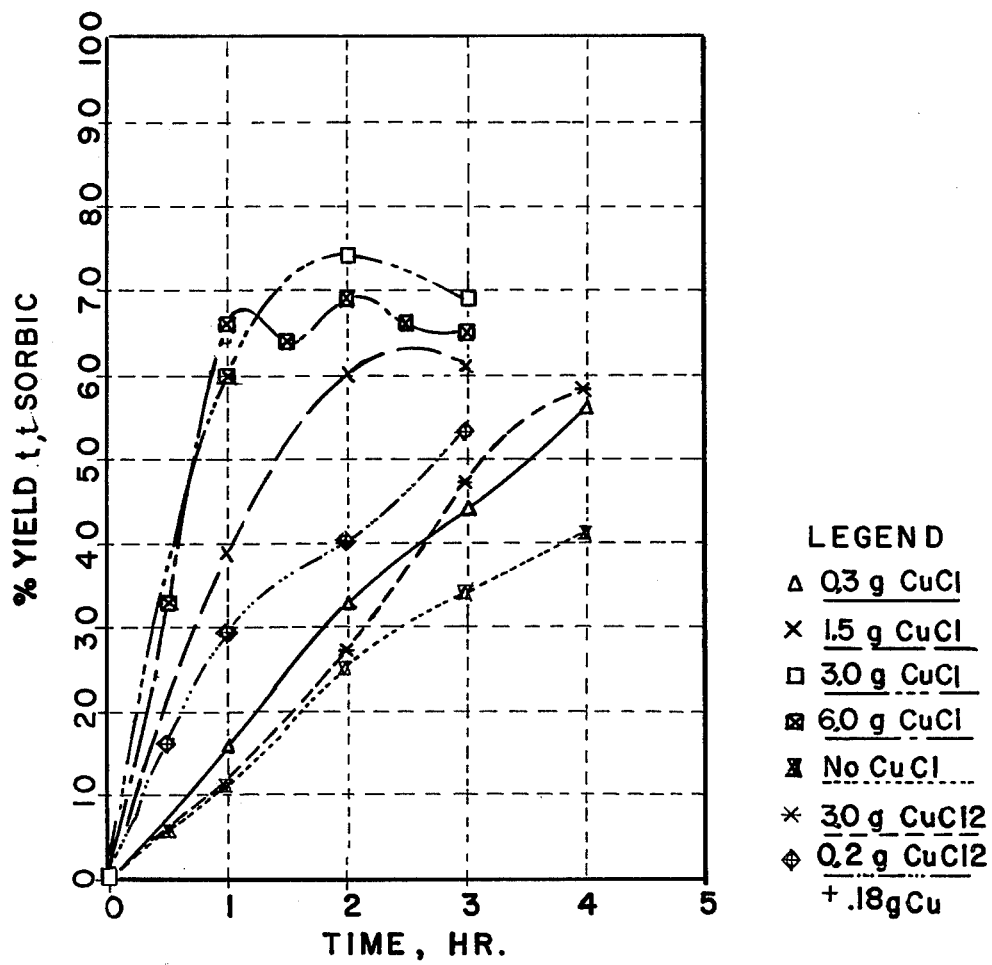

United States Patent [19]
Coleman et al.

[11] Patent Number: 4,460,787
[45] Date of Patent: Jul. 17, 1984

[54] METAL AND ACID CATALYSIS IN SORBIC ACID PREPARATION

[75] Inventors: James P. Coleman; Richard C. Hallcher, both of Maryland Heights, Mo.

[73] Assignee: Monsanto Company, St. Louis, Mo.

[21] Appl. No.: 332,393

[22] Filed: Dec. 21, 1981

[51] Int. Cl.$^3$ .................. C07C 51/09; C07C 51/377; C07C 57/10
[52] U.S. Cl. .................... 562/599; 549/326; 560/241; 562/600; 562/601
[58] Field of Search .............................. 562/599, 601

[56] References Cited
U.S. PATENT DOCUMENTS 4,022,822 10/1977 Tsujino et al. ...................... 562/601
4,158,741 6/1979 Goi et al. ............................ 562/599
4,296,243 10/1981 Sato .................................... 562/599

FOREIGN PATENT DOCUMENTS 38-19106 9/1963 Japan ................................. 562/601

Primary Examiner—Vivian Garner
Attorney, Agent, or Firm—Joseph D. Kennedy; James W. Williams, Jr.

[57] ABSTRACT

The acid conversion of certain precursors, e.g. γ-vinyl-γ-butyrolactone, to sorbic acid is improved by presence of copper or silver ions along with the acid.

11 Claims, 1 Drawing Figure

METAL AND ACID CATALYSIS IN SORBIC ACID PREPARATION

The present process concerns the use of copper or silver catalyst in the conversion of γ-vinyl-γ-butyrolactone and other sorbic acid precursors to sorbic acid.

BACKGROUND OF THE INVENTION

Sorbic acid is a known material which is useful as a food preservative and for related purposes.

It is known that γ-vinyl-γ-butyrolactone can be converted to sorbic acid through the use of acids or various catalytic materials as disclosed in U.S. Pat. Nos. 4,022,822 and 4,158,741. It is also known that sorbic acid is commercially manufactured by reacting crotonaldehyde with ketene to produce a polyester which can be converted to sorbic acid with use of acid or base. The use of copper ions along with manganese ions has been described in reactions of olefins and acetic acid to produce unsaturated acids, see U.S. Pat. No. 3,927,051.

In addition, commonly assigned application Ser. No. 222,200, filed Jan. 2, 1981, U.S. Pat. No. 4,356,317, of Coleman, Hallcher and McMackins describes the use of copper ions along with manganese in a procedure for producing acetoxyhexenoic acids from butadiene and acetic acid, particularly a mixture of 6-acetoxy-4-hexenoic acid and 4-acetoxy-5-hexenoic acid.

SUMMARY OF THE INVENTION

The present invention involves a procedure for using copper or silver, in conjunction with acid, to convert sorbic acid precursors to sorbic acid. The invention includes the use of copper or silver and acid to convert γ-vinyl-γ-butyrolactone to sorbic acid, or to convert the polyester obtained from ketene and crotonaldehyde to sorbic acid. It also includes use of copper or silver and acid to convert acetoxyhexenoic acids to sorbic acid.

Sorbic acid precursors include acetoxyhexenoic acids, polyester of 3-hydroxy-4-hexenoic acid and γ-vinyl-γ-butyrolactone. Another precursor which can be used is 5-hydroxy-3-hexenoic acid lactone, and other materials capable of conversion to sorbic acid by contact with acid can be used in the present invention.

A broad variety of acids and acidic materials are effective in causing conversion of precursor materials to sorbic acid. However, a number of common acids, e.g. hydrochloric acid, give very poor reaction rates and appear impractical for use alone with some precursors.

It has now been found that the effect of such materials is augmented by copper or silver, particularly by cuprous ion or argentous ion. The use of cuprous ion serves to accelerate the reaction, producing more sorbic acid in shorter contact times.

The process to convert γ-vinyl-γ-butyrolactone or other precursor to sorbic acid will generally involve contacting the lactone or other precursor with acid and copper ion at elevated temperature. Strong acids in general can be used in the present invention, e.g. mineral acids, aromatic sulfonic acids, aliphatic sulfonic acids, etc., such as hydrochloric acid, sulfuric acid, phosphoric acid, p-toluenesulfonic acid, methane sulfonic acid, etc. Hydrochloric acid is preferred and some of the other acids may present problems of solubility of the copper salts. Secondly, acid ion exchange resins, e.g. sulfonated polystyrenes can be used but care should be taken that the amount of copper ion is not sufficient to neutralize all of the acid sites. The function of the acids is apparently to supply hydrogen ion which catalyzes the conversion to sorbic acid. Thus the present invention can be viewed as involving a catalysis by hydrogen and cuprous ions or argentous ions.

The present process is generally conducted at elevated temperature in order to promote the reaction, although the formation of sorbic acid occurs to some extent even at ambient temperatures. The contact of the lactone or other precursors will generally be carried out at temperatures from about 30° to about 150° or 200° C., preferably from about 60° to about 140° C. Operation in the range of about 80° to 110° gives fairly good reaction rates. If necessary, pressurized equipment can be used to avoid loss of reaction components or solvent, but it will often be more convenient to operate below the boiling point of the components or reaction mixture involved, or possibly at reflux conditions.

The reaction rate will vary with the amount of cuprous ion present and, to a lesser extent, with the amount of acid. The amount of copper salt, calculated on the basis of copper, will generally be in the range of about 2% to 40% by weight of the lactone or other sorbic acid precursor, usually in the range of about 10% to 30% by weight. The same amounts of silver may be used, although there may be a preference for use of higher amounts of silver because of lower effectiveness in the present process. Of course, lesser, or any significant amounts of copper will have some effect, and amounts greater than 40% by weight can also be used, although not usually providing any additional advantage.

The concentration and amount of acid can be selected to give good reaction rates. In general, an equimolar or greater amount of acid for the lactone or other precursor is preferred but lesser amounts can be used. The amount of acid to sorbic acid precursor will often range from about equimolar up to a 5 molar ratio of the acid to precursor, but lesser amounts of the acid may be employed, e.g. ranging upwards from about 0.25 molar amounts per mole of precursor. Since the acid can be reused, small amounts can be used but the rate is better with high amounts. In the absence of copper salts, concentrated hydrochloric or other acids give better reaction rates than dilute acids, but with the use of copper salts, dilute acids give satisfactory rates, e.g. concentrations of 15% to 30% or so by weight, particularly with hydrochloric acid. With hydrochloric acid, concentrations, e.g. from 5% up to the commercially available concentrated hydrochloric acid, about 36%, can be used, e.g. about 10% to about 30%. There may be some advantage in cost or convenience in using dilute rather than concentrated acids, and the present invention makes it feasible to utilize dilute acids and still obtain good reaction rates. It will be recognized, of course, that acids should not be employed which interfere significantly with the desired reaction or cause substantial degradation of the reactant or products.

The temperature, cuprous ion concentration, and acid concentration all have an influence on the reaction rate, and these can be combined to give desired rates. For example, if a particular copper concentration and dilute acid give a slightly lower rate than desired, the temperature may be increased to provide the desired rate. The reaction rate generally increases with temperature, but there is more of a tendency toward product degradation at higher temperatures. In batch reactions, it will generally be desirable to select conditions which produce 60 to 70% or better yields of sorbic acid in one hour or less.

Ordinarily, it will be convenient to use an aqueous mineral acid in the present procedure. The γ-vinyl-γ-butyrolactone or other sorbic acid precursor can be added directly to the aqueous acid, containing cuprous chloride or other cuprous salt. Solubility of the lactone is sufficient to obtain good reaction, and the sorbic acid will readily precipitate from most aqueous acids. However, if desired, the lactone can be dissolved in an organic solvent, e.g. a hydrocarbon or halogenated hydrocarbon, and the resulting solution can be brought into contact with the aqueous acid in a two-phase system. There is usually no substantial difference in yields in the two procedures, but the product isolated from the organic solvent is less apt to be contaminated with acid, high boiling products, or copper salts. Also, a two-phase system is useful when utilizing a continuous crystallization procedure to separate the sorbic acid product as the reaction occurs and improve selectivity to the acid. While this crystallization procedure is exemplified in one of the examples herein, it is further described in a simultaneously filed, commonly assigned copending application of one of U.S. Ser. No. 332,391 filed Dec. 21, 1981.

Among other organic solvents which may be found convenient for use in the present invention are alkanoic acids, particularly lower alkanoic acids, e.g. acetic acid. Acetic acid is a reactant in procedures for preparing acetoxyhexenoic acids, as discussed hereinabove with respect to a commonly assigned application Ser. No. 222,200, and also in procedures for preparing γ-vinyl-γ-butyrolactone, and therefore it may be convenient to have it present in the present process.

The copper utilized in the present invention is effective primarily in the form of cuprous ion, i.e. copper I ion, but can be supplied in a form capable of forming copper ion in solution. Soluble copper salts, such as those soluble in water or mineral acids, are particularly convenient for use, e.g. copper chlorides, copper nitrates, etc. Cuprous oxide can also be used. It is often convenient to use the copper salt of the acid being used in the procedure. Copper hydroxides can be used, but will react with the acid employed, requiring use of additional acid reagent. Copper in monovalent form appears to be more effective than divalent copper, and it may be that the divalent copper has effect only by some presence of copper I, or through some conversion to copper I. Thus the copper can be supplied partly as zero-valent copper powder and partly as a cupric salt, resulting in an oxidation-reduction to form copper I. Copper can be supplied in the zero-valent state and oxidized in situ to copper I, or in the divalent state and reduced in situ to copper I. Silver can similarly be supplied in various forms, e.g. as soluble salts, e.g. as silver acetate or silver nitrate, and can be oxidized or reduced in situ to the desired valence. Silver is effective in mono-valent form.

EXAMPLE 1

A 10 gram amount of γ-vinyl-γ-butyrolactone was placed in a vessel with 240 grams iso-octane and 60 grams of 25% by weight hydrochloric acid and heated to 87° C. while the conversion to sorbic acid was monitored. The same procedure was carried out, but with various designated amounts of copper chlorides present, and the yields of trans, trans-sorbic acid were plotted on a time basis in hours, as illustrated in FIG. 1. It can be seen that the reaction was very slow in the absence of added copper, producing slightly better than a 40% yield in 4 hours. In contrast to this, the addition of 3 grams cuprous chloride gave better than a 70% yield in 2 hours. It can be seen that the presence of 1.5 to 6 grams of cuprous chloride caused a very marked improvement in reaction rate, in such cases producing better than 60% yields in 3 hours, while a 0.3 gram amount of cuprous chloride had a less pronounced effect. A 3 gram amount of cupric chloride resulted in some improvement, but the effect was similar to that of only 0.3 gram cuprous chloride. When a 0.2 gram amount of cupric chloride was employed with 0.18 gram copper metal powder, a fairly good improvement in rate was noted, with better than 50% yield in 3 hours; the presence of both cupric and zero-valent copper permits an oxidation-reduction reaction to provide cuprous ion with a resulting effect on the production of sorbic acid.

EXAMPLE 2

Provisions were made for reaction of γ-vinyl-γ-butyrolactone in a two-phase system in which the lactone in isooctane was continuously cycled to contact with an aqueous hydrochloric acid, and separated therefrom, with a stage for crystallization of the sorbic acid product from the isooctane phase. A 3 gram amount of cuprous chloride was used with 29 grams of 25% hydrochloric acid. The amount of isooctane was 325 ml, and the reaction temperature was 86° C., while cooling was employed to effect crystallization of the sorbic acid product. Four runs were made in series, each employing 22.4 grams of the lactone, with results as reported in Table 1. The cumulative molar ratio of lactone to hydrochloric acid changed from 1/1 to 4/1 over the four runs, with no strong effect on results.

TABLE 1

| Run # | Lactone (g) | Yield % | Conc. Sorbic end of run | Addition* time, hrs. | Molar Ratio lactone/HCl |
|---|---|---|---|---|---|
| 1 | 22.4 g | 81 | 1.4% | 3.75 | 1/1 |
| 2 | " | 93 | 1.0% | " | 2/1 |
| 3 | " | 88 | .9% | " | 3/1 |
| 4 | " | 84 | 1.4% | " | 4/1 |

*Runs continued for 1 hour after addition

The sorbic acid was crystallized from solution as formed, leaving only a small amount of sorbic in solution at the end of the runs. Good yields of sorbic acid were obtained. A two-phase system for crystallization as employed in this procedure is further described in commonly assigned copending application, Ser. No. 332,391.

EXAMPLE 3

A polyester obtained by reaction of ketene and crotonaldehyde was employed as sorbic acid precursor in this example. A 19.13 gram amount of the polyester was added to 25% hydrochloric acid (30 grams), and 2.5 grams cuprous chloride. The mixture was stirred at 90° C. for 30 minutes, and the pasty reaction mixture was then cooled and filtered to separate crystals of sorbic acid. The crystals were dissolved in acetone and analyzed by chromatography (in silated form with benzophenone as internal standard), for a 90% yield of trans, trans-sorbic acid.

The procedure of Example 3 was repeated but without cuprous chloride. After 30 minutes, only a 19% yield of sorbic acid was obtained.

The polyester employed in Example 3 is a polymer of 3-hydroxy-4-hexenoic acid, as produced by the reaction of ketene and crotonaldehyde in a known industrial process for producing sorbic acid.

EXAMPLE 4

Reactions were carried out in a reaction vessel containing 10 grams of γ-vinyl-γ-butyrolactone and 15 grams of 25% by weight hydrochloric acid, with heating at 85° C. Different amounts of cuprous chloride were employed with selected reaction times for each amount to provide data to plot the yield of sorbic acid vs. time for each amount. The yields of sorbic acid were determined by cooling the reaction mixture to room temperature after the designated time, removing the trans, trans-sorbic acid by filtration and determining its amount by gas chromatography. The approximate yields at designated reaction times are reported in Table 2. The higher yields reported with each amount are approximately the maximum of the time yield plots for such amounts.

TABLE 2

| Amount CuCl (grams) | Yield t, t-sorbic acid Time | | | | | |
|---|---|---|---|---|---|---|
| | 1 hr. | 2 hrs. | 1.5 hrs. | 2.5 hrs. | 3.5 hrs. | 6 hrs. |
| 2.5 | 70 | | 80 | | | |
| 1.9 | 60 | | | 85 | | |
| 1.25 | 40 | | 60 | | 87 | |
| 0.63 | | 38 | | | | 87 |

EXAMPLE 5

A 10 gram amount of γ-vinyl-γ-butyrolactone was heated at 87° in a reaction mixture containing 5 grams silver acetate, 60 grams 25% hydrochloric acid, and 240 grams isooctane. The reaction mixture involved an upper organic phase and a lower aqueous-acid phase, with the phase being mixed by stirring during the reaction period. The amount of trans, trans-sorbic acid in the upper layer was measured. The yield of sorbic acid approached 30% in less than one-half hour, and was over 50% at the end of three hours. This was much faster than the rate without the silver acetate, the yield being slightly over 30% at 3 hours with only the hydrochloric acid as catalyst. The silver acetate was less effective than cuprous chloride, as a comparable procedure but with 3 grams cuprous chloride in place of the silver acetate, gave approximately a 75% yield in two hours.

Acetoxyhexenoic acids will ordinarily be the acyloxyhexenoic acids used herein if acyloxyhexenoic acids are used rather than vinylbutyrolactone, etc. Acetoxyhexenoic acids are convenient in preparation, particularly as a mixture of 6-acetoxy-4-hexenoic acid and 4-acetoxy-5-hexenoic acid, and readily converted in the present process. Therefore, there is ordinarily no need to use other acyloxy groups. However, other acyloxyhexenoic acids can, if desired, be converted to sorbic acid in the present process, particularly 6-acyloxyhexenoic acid and 4-acyloxy-5-hexenoic acid or mixtures thereof. Acyloxy groups of various chain lengths can be used, but it will usually be convenient to use lower acyloxy groups, such as those of 2 to 6 carbon atoms, being the acyloxy moiety of lower alkanoic acids.

EXAMPLE 6

Acetoxy acids (15.4 g) were heated at 90° C. in the presence of hydrochloric acid (15 g. 25%) and CuCl (1.25 g) for 4 hours. The mixture was cooled and the sorbic acid was filtered. Analysis showed a 54% yield of trans, trans-sorbic acid.

EXAMPLE 7

Acetoxy acids (15.4 g.) were heated at 87° in the presence of hydrochloric acid (60 g. 25%) CuCl (3 g.) and isooctane (240 g.) for 4 hours. Analysis of the isooctane showed a 73% yield of trans, transsorbic acid. The acetoxy acids utilized were a mixture of 6-acetoxy-4-hexenoic acid and 4-acetoxy-5-hexenoic acid.

As discussed herein, various sorbic acid precursors can suitably be employed in the present process. This is true even though the rates may vary somewhat with the precursor, and even though hydrochloric acid alone is more effective with polyester than with γ-vinyl-γ-butyrolactone. Thus the choice of precursor depends to a great extent on availability of particular precursors, which may thus depend upon the relative merits of preparation processes therefor and availability and cost of reactants therein. However, some processes are capable of operation or modification to be directed toward production of either acetoxyhexenoic acids or γ-vinyl-γ-butyrolactone, as noted in the aforesaid Ser. No. 222,200, and if such processes prove most efficient for lactone production, the lactone is then likely to be preferred over the acetoxy-acids in the present process.

What is claimed is:

1. In the process of converting sorbic acid precursors selected from the group consisting of acyloxyhexenoic acids, polyester of 3-hydroxy-4-hexenoic acid, γ-vinyl-γ-butyrolactone and 5-hydroxy-3-hexenoic acid lactone to sorbic acid by contact with strong acids, the improvement of using cuprous or argentous ions in conjunction with strong acid.

2. The process of claim 1 in which a mineral acid is employed.

3. The process of claim 1 in which the acid is hydrochloric acid.

4. The process of claim 1 in which hydrochloric acid of less than 30% concentration is employed.

5. The process of converting sorbic acid precursors selected from γ-vinyl-γ-butyrolactone, acetoxyhexenoic acids and polyester of 3-hydroxy-4-hexenoic acid to sorbic acid which comprises contacting such precursor with strong acid and cuprous or argentous ion at temperatures in the range of about 30° to about 200° C.

6. The process of claim 5 in which the precursor is γ-vinyl-γ-butyrolactone.

7. The process of claim 5 in which the precursor is polyester obtained by the reaction of ketene and crotonaldehyde.

8. The process of claim 5 in which the precursor is a mixture of 6-acetoxy-4-hexenoic acid and 4-acetoxy-5-hexenoic acid.

9. The process of claim 5 in which hydrochloric acid of concentration in the range of about 10% to about 30% is employed with cuprous ion to convert γ-vinyl-γ-butyrolactone to sorbic acid.

10. The process of claim 5 in which the precursor is heated at temperatures in the range of about 60° to about 140° C. in the presence of cuprous or argentous ions.

11. The process of claim 10 in which cuprous ion is present in a concentration in the range of about 2% to 40% by weight of the sorbic acid precursor.

* * * * *